(12) United States Patent  
Ellman et al.

(10) Patent No.: US 7,094,231 B1  
(45) Date of Patent: Aug. 22, 2006

(54) DUAL-MODE ELECTROSURGICAL INSTRUMENT

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 349 days.

(21) Appl. No.: 10/761,774

(22) Filed: Jan. 22, 2004

(51) Int. Cl.
*A61B 18/18* (2006.01)

(52) U.S. Cl. .............................. 606/37; 606/34; 606/39; 606/40

(58) Field of Classification Search ............ 606/32–34, 606/37–42
See application file for complete search history.

(56) References Cited

U.S. PATENT DOCUMENTS

| | | | | |
|---|---|---|---|---|
| 4,071,028 A | * | 1/1978 | Perkins .......................... | 606/37 |
| 4,171,700 A | * | 10/1979 | Farin ............................. | 606/35 |
| 5,562,503 A | * | 10/1996 | Ellman et al. ............... | 439/638 |
| 5,613,966 A | * | 3/1997 | Makower et al. ............. | 606/34 |
| 5,954,686 A | * | 9/1999 | Garito et al. .................. | 604/37 |
| 6,113,596 A | * | 9/2000 | Hooven et al. ................ | 606/42 |
| 6,830,569 B1 | * | 12/2004 | Thompson et al. ........... | 606/34 |
| 6,994,707 B1 | * | 2/2006 | Ellman et al. ................. | 606/42 |
| 2004/0054365 A1 | * | 3/2004 | Goble .......................... | 606/34 |

* cited by examiner

*Primary Examiner*—Michael Peffley (57) ABSTRACT

An electrosurgical instrument that is capable of generating high-quality RF energy at a single frequency in the MHz range best suited for delicate, precise and quick-healing cutting procedures with low leakage currents using a monopolar handpiece, and also provides high-quality RF energy at the same frequency suited for use for carrying out similar procedures for use with a bipolar handpiece. In a preferred embodiment, the instrument is capable of generating sub-modes of electrosurgical currents with different waveforms optimized for cutting and hemostasis, and the various sub-modes are available for both the monopolar and bipolar handpieces. A preferred operating frequency is in the range of 4 MHz. The instrument includes means for maintaining a substantially constant power output irrespective of selection of one of the sub-modes.

17 Claims, 4 Drawing Sheets

DUAL-MODE ELECTROSURGICAL INSTRUMENT

The invention is directed to an electrosurgical instrument or apparatus, and in particular to an electrosurgical instrument that operates in both the monopolar and bipolar modes.

BACKGROUND OF INVENTION

Electrosurgical instruments are well known and widely used in the medical, dental, and veterinarian fields. They offer the capability of precision cutting with electrosurgical currents in the megacycle range using a handpiece with needle, ball, or loop electrodes in a main monopolar operating mode, or convenient coagulation (hemostasis) using a forceps in a main bipolar operating mode. Ellman International, Inc. makes available an electrosurgical instrument which provides on its front panel connectors for receiving the plug of a monopolar handpiece and a ground or indifferent plate, as well as connectors for receiving the plug of a bipolar forceps.

In a common surgical setting, a surgeon may first use the monopolar handpiece to perform a desired cutting procedure and then desire to use the bipolar forceps for coagulation of blood vessels because of its unique ability to coagulate in a fluid field. This creates problems in maintaining the requisite sterile field while still allowing the surgeon to unplug and plug in different devices from or to the instrument. One possible solution is described in U.S. Pat. No. 5,562,503, whose contents are herein incorporated by reference. In the solution proposed in this patent, an adaptor apparatus is provided and configured to plug directly into the connectors on the electrosurgical instrument, and provided with connector means for receiving mating connectors of both the monopolar handpiece and the bipolar forceps. Switch means are provided on the adaptor apparatus for allowing the surgeon to easily switch over from the monopolar to the bipolar mode by simply throwing the switch while maintaining a sterile field. However, the instrument described in this patent uses a single low frequency for the operating modes when using either a monopolar handpiece or a bipolar handpiece with the latter receiving only coagulation currents. This is not always optimum for both cutting and hemostasis. Moreover, many procedures are optimized when employing radio-frequency (RF) electrosurgical currents in the 4 MHz range, which thus requires an instrument which provides 4 MHz energy for delicate, precise and quick-healing cutting procedures, but with low leakage currents.

Moreover, under certain circumstances, it has sometimes been found that low frequency monopolar electrosurgery can cause sparking, current spread, and excessive thermal damage in the tissue because of the excessive generation of heat. Especially, this can result in deleterious effects to the tissue in proximity to the operative site in working around metal objects such as orthopedic implants, surgical screws, craniofacial metal plates and recently dental implants, thus creating the potential for electrical shock, osteoradionecrosis, and subsequent rejection of the metal implant. High frequency (3.8 to 4 MHz) energy has been proven to greatly reduce the sparking and deleterious effects of typical low frequency electrosurgical devices.

Our prior U.S. Pat. No. 5,954,686, whose contents are incorporated herein by reference, describes a novel electrosurgical instrument that provides RF energy in the 4 MHz range for the monopolar mode but a lower frequency for the bipolar mode in order to realize satisfactory hemostasis functionality. Moreover, as with the earlier instruments, only hemostasis electrosurgical currents are available in the bipolar mode. While the use of bipolar electrosurgery that employ bipolar handpieces with coaxial electrodes or parallel needles or balls for localizing the electrosurgical currents between the electrodes can reduce the deleterious effects described above, to the best of our knowledge, all bipolar electrosurgery designed for cutting operate at frequencies below 1 MHz and are not able to smoothly and precisely cut soft tissue.

To the best of our knowledge, there is no commercially-available instrument that provides high output radio-frequency (RF) energy for delicate, precise, and quick-healing cutting procedures with low leakage currents that provides multiple sub-modes of RF energy for both a monopolar handpiece and a bipolar handpiece.

SUMMARY OF INVENTION

The principal object of the invention is an electrosurgical instrument capable of providing optimal RF energy for both cutting and hemostasis using either the main monopolar or bipolar mode of the instrument.

Another object of the invention is an electrosurgical instrument capable of providing multiple electrosurgical currents for both cutting and hemostasis using either the monopolar or bipolar mode of the instrument.

A further object of the invention is an electrosurgical instrument capable of providing RF energy output adjustable to the same high power level in the 4 MHz range for both cutting and cutting/coagulation using either the monopolar or bipolar mode of the instrument.

These objects are achieved in accordance with one aspect of the invention by an electrosurgical instrument that is capable of generating RF energy in the 4 MHz range with low leakage currents suited for delicate, precise, and quick-healing cutting procedures and hemostasis using a monopolar handpiece, and also is capable of generating RF energy in the 4 MHz range with low leakage currents suited for delicate, precise, and quick-healing cutting procedures and hemostasis using a bipolar handpiece.

In a preferred embodiment, the electrosurgical instrument of the invention is provided with output connectors for receiving, respectively, monopolar and bipolar handpieces, and circuitry that enables a surgeon to operate the instrument to deliver approximately 4.0 MHz energy in three different sub-modes to each of the output connectors.

In accordance with a further aspect of the invention, the instrument is configured so that both a monopolar handpiece and a bipolar handpiece can be used during a surgical procedure, though not at the same time, without having to activate any switches on the instrument. This has the advantage of providing the surgeon all the benefits of both main electrosurgical modes while not jeopardizing the crucial sterile field.

Our novel monopolar/bipolar 4 MHz high frequency electrosurgical currents produce very low tissue temperatures. Both the monopolar side and bipolar side deliver three distinctly different current waveforms, which produce different histological effects on soft tissue. In either monopolar or bipolar, the surgeon can have cut, cut and coagulation, and hemostasis electrosurgical currents in the 4 MHz range, giving the surgeon the selection of waveforms to produce the different histological effects preferred for the different procedures to be implemented.

The bipolar mode of the instrument of the invention utilizes a handpiece with two metal electrodes in close proximity. One of the metal electrodes acts as the active energy electrode and the other acts as the passive electrode. In this system configuration, the RF current flows from an active electrode through a very discrete area of tissue and back into the adjacent passive electrode completing the circuit to the power unit. This results in an extremely limited area of therapeutic action and does not require the current to be dissipated through the patients' general body tissue in order to reach the return electrode pad as in monopolar operation. Only tissue between the two electrodes is part of the conductive pathway. In addition to thus localizing the electrosurgical action, we have found that bipolar energy in the 4 MHz range greatly reduces or eliminates the potential patient damage arising from the presence of metal implants and screws and other conductive devices such as implanted pacemakers and defibrillators.

A further feature of the invention is the independent control of the main monopolar and bipolar modes to obtain substantially the same maximum output power irrespective of the cutting or cutting/coagulation sub-mode selected.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

The invention is intended for use with conventional monopolar electrodes having points, needles, balls, wires, and scalpel and curette blades, as examples, as well as with bipolar electrodes of the conventional forceps type, as well as with bipolar probes of the types shown in U.S. Pat. Nos. 6,231,571; 6,572,614; 6,620,156; and similar types involving multiple needles or coaxial structures, as examples. The contents of these referenced patents are incorporated herein by reference. The invention is especially important for use with RF electrosurgical currents in the 4 MHz range as our experience has shown that 4 MHz frequency energy used in the main monopolar mode produces excellent cutting ability through soft tissue. Especially is this important with bipolar electrodes in the main bipolar mode, because the same smooth cutting occurs with the added safety of eliminating the indifferent plate and localizing the electrosurgical currents to the region between the two bipolar electrodes.

The three different electrosurgical waveforms traditionally available in the monopolar mode, in accordance with the invention, are now available also in the bipolar mode. These three waveforms, termed herein operating sub-modes, are known as:

1. Partially Rectified: Moderately damped waveform or half wave current on tissue. This typically produces a hemostasis effect on soft tissue.

2. Fully Recified: Undamped electronic current waveform. This is typically a cut and coagulation blend.

3. Continuous Wave: Fully Filtered current waveform. Typically this is pure smooth cutting with little hemostasis.

These waveforms are shown by the solid lines in U.S. Pat. No. 3,730,188 in, respectively, FIGS. 5c, 5b, and 5a.

Thus, in the invention, the 4 MHz frequency energy is available in the three most popular waveforms in both monopolar and bipolar. This now makes six distinctly different waveforms available to the surgeon, meaning six different therapeutic currents which produce different histological effects on the soft tissue.

Figure 1:
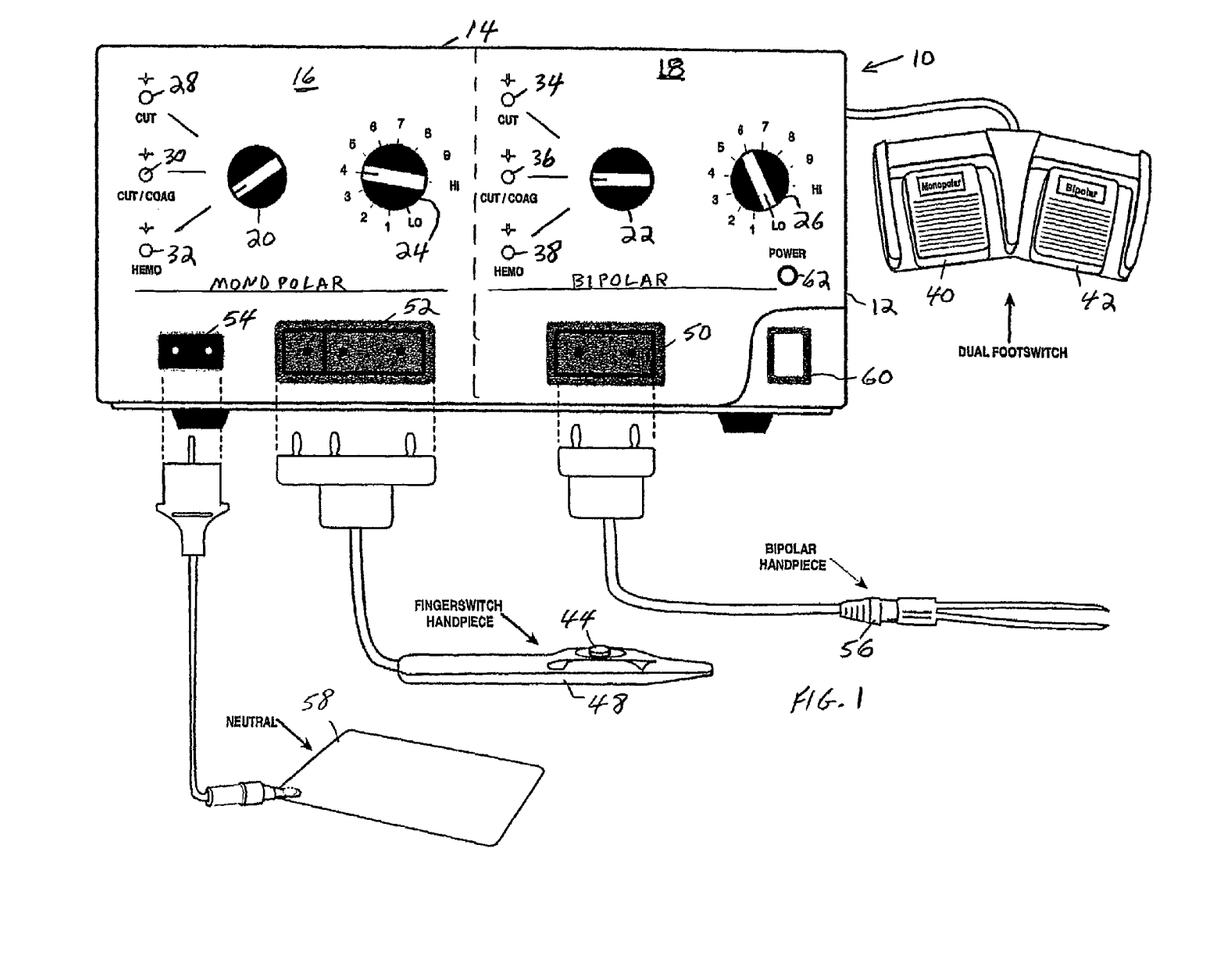
FIG. 1 is a front panel partially schematic view of one form of electrosurgical instrument in accordance with the invention.

One form of the electrosurgical instrument 10 according to the invention is illustrated in FIG. 1. It comprises a console unit having a box-like housing 12 comprising at the front a control panel 14 for the instrument. The control panel 14 is divided into two halves, as indicated, the one/half 16 on the left as marked to indicate monopolar operation, and the one/half 18 on the right marked to indicate bipolar operation. Each half includes a 3-position sub-mode control switch 20, 22, respectively, and a multi-positional variable power switch 24, 26, respectively. Each half also includes indicator lights 28, 30, 32, respectively, 34, 36, 38 labeled CUT, CUT/COAG, HEMO, respectively. When the sub-mode control switch 20, 22 is in the CUT position, the corresponding light 28, 34 is ON and the Continuous Wave: Fully Filtered current waveform is generated. When the sub-mode control switch 20, 22 is in the CUT/COAG position, the corresponding light 30, 36 is ON and the Fully Recified: Undamped waveform is generated. When the sub-mode control switch 20, 22 is in the HEMO position, the corresponding light 32, 38 is ON and the Partially Rectified: Moderately damped waveform is generated. When the respective sub-mode control switch, 20, 22 is pointing at one of the indicator lights, then internal circuitry causes that indicator to turn ON and the other indicators to turn OFF. As will be explained below, the choice of which half of the instrument is active depends entirely on which of three active external controls are activated; two of the active controls comprising footswitches 40, 42 and the third fingerswitch 44 on the fingerswitch handpiece 48.

The two power switches 24, 26 control the power output, respectively, for the main monopolar and bipolar modes of operation. No actual power output in watts is given; instead the controls indicate values from LO to HI on a scale of 1–10. Through experience, each surgeon comes to know the appropriate power level represented by the position of the power output knob to choose for a particular procedure. At the bottom of the unit are output female connectors 50, 52, 54 for plugging in, respectively, at the right, a bipolar handpiece or forceps 56, a fingerswitch-controlled monopolar handpiece 48 at the center, and at the left a single or split neutral plate 58. Note that the respective female connectors are positioned underneath the appropriate half of the front panel. Thus, the bipolar connector 50 is under the bipolar half of the panel 18, and the two monopolar connectors 52, 54 are under the monopolar half of the panel 16. An on-off power switch 60 with its accompanying indicator light 62 is at the far right. The circuitry used to provide a fingerswitch-controlled monopolar handpiece may be of the type described in connection with the control unit 50 of U.S. Pat. No. 4,463,759, whose contents are herein incorporated by reference, which circuitry is in this case incorporated in the console unit 12. A connector (not shown) is provided at the right side for receiving a dual conventional footswitch 40, 42. A feature of the invention is that both the monopolar and bipolar handpieces can be simultaneously connected to the console unit 12 and operated in any order without touching the console unit or the control panel when the control panel has been preset or activated at the desired powers for each of the handpieces.

For example, if the surgeon determines that s/he is going to perform a cutting procedure with a particular electrode, then s/he can preset the cutting mode power for, for example, the fingerswitch handpiece 48 using the monopolar power control 24. For hemostasis with the bipolar forceps 46, s/he may desire to use a lower power level, which can also be preset using the monopolar power control 26. The internal circuitry is controlled so that, when the fingerswitch monopolar handpiece 48 is used, then RF power can be supplied to the electrode in the monopolar handpiece when a fingerswitch 44 on the handpiece 48 is depressed or the monopolar footswitch 40 is operated. However, when it is desired to use the bipolar handpiece 56, then the footswitch 42 is depressed, which then supplies RF power to the forceps of the bipolar handpiece. As an example only, these units can be designed to supply up to about 50–60 watts of RF power to either handpiece. Typically, again only as an example, about 30–60 watts may be typically used in the CUT sub-mode; about 20–60 watts may be typically used in the CUT/COAG sub-mode; and about 5–20 watts may be typically used in the HEMO sub-mode. This result is a consequence of hardwired circuitry such that, when the bipolar footswitch 42 or the bipolar handpiece 56 is operated, RF power is supplied only to the bipolar connector 50; and when the monopolar footswitch 40 or the monopolar handpiece 48 is operated, RF power is supplied only to the monopolar connectors 52, 54. This prevents power selected for the monopolar handpiece to be applied to the bipolar handpiece, and vice-versa.

Figure 2A:
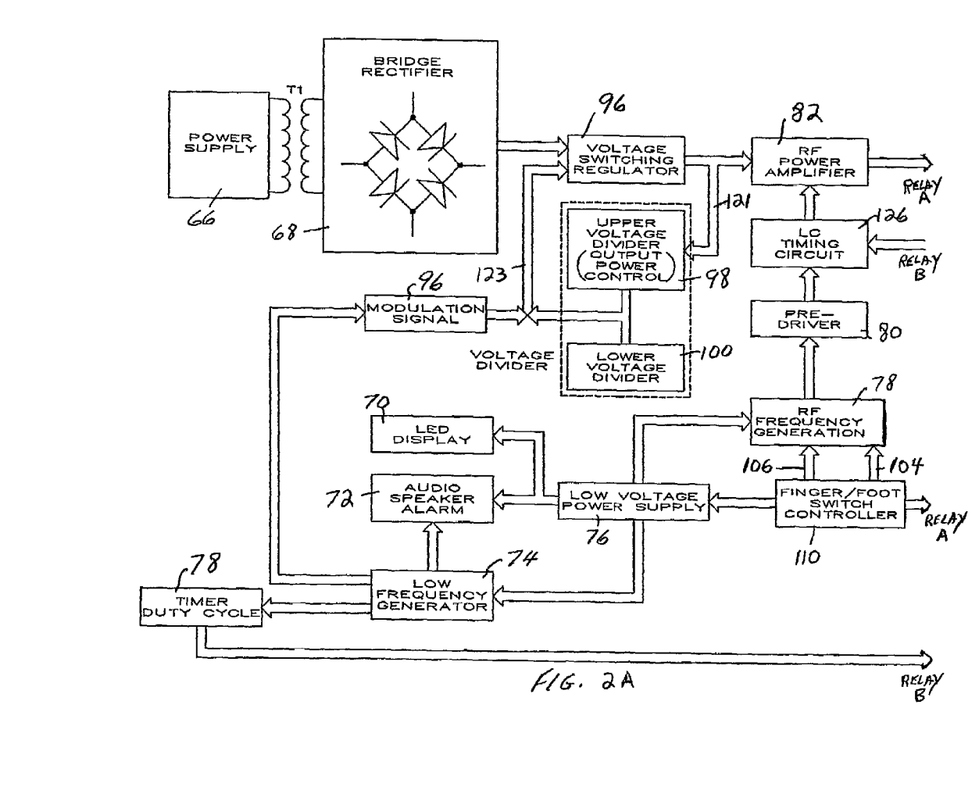
FIGS. 2A and 2B are a circuit block diagram of one form of system circuitry for the electrosurgical instrument of FIG. 1.
Figure 2B:
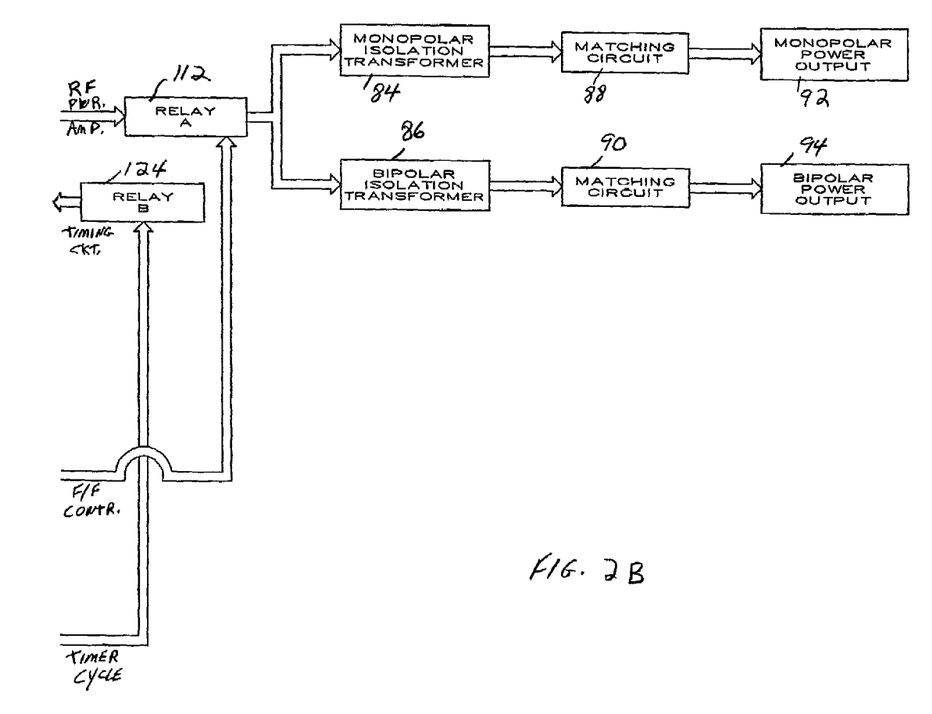

One form of the RF circuitry to achieve the foregoing operation is illustrated in the block diagrams of FIGS. 2A and 2B. As will be observed, FIG. 2B is an extension of FIG. 2A as indicated by the labels. There are several similar circuit modules or blocks in the present circuit and that illustrated and described in U.S. Pat. No. 5,954,686 ('686), previously incorporated by reference which also provides monopolar and bipolar outputs. But there are also significant similarities between certain modules in U.S. Pat. No. 6,238,388 ('388), hereby incorporated by reference, and those of the present invention, except that the latter patent provides only a monopolar output. Those similarities will be briefly pointed out when the block diagram of the present invention is described, and mainly the significant differences will be explained in detail.

In the present invention, referring now to FIG. 2A, the power supply 66 and bridge rectifiers 68 are similar to the corresponding modules in FIG. 3 of the '686 patent. The LED display module 70, which supplies the power to the respective indicator lights, the audio speaker alarm module 72, which supplies a safety function to warn the surgeon when a reasonable procedure duration has been exceeded, the low frequency generator 74 which supplies the audio tone as well as a counting frequency for the timer duty cycle module 78, which is also part of the safety framework for the surgeon, are all powered by the low voltage power supply module 76. These modules 70, 72, 74, 76, 78 are all conventional and their construction will be apparent to the skilled person in this art. The RF frequency generator 78, the pre-driver 80, and the RF power amplifier 82 are also conventional and similar to corresponding modules in FIG. 3 of the '686 patent, except that only a single RF frequency carrier having a frequency of the order of 4 MHz is generated. In the FIG. 2B extension, note that there is an independent chain of isolation transformer 84, 86, matching circuit 88, 90, and power output 92, 94 for each of the main monopolar and bipolar modes. Again, these circuits are similar to the corresponding modules in FIG. 3 of the '686 patent except that, again, the same 4 MHz current is supplied to both outputs and so the impedance matching is the same for both chains. The respective outputs 92, 94 are connected to their corresponding connector 52, 50. The main difference between the two chains is that the bipolar chain is completely isolated whereas the monopolar chain is grounded for the neutral connection 54.

In the modules so far described, the circuit details are not important because there are a number of different ways to achieve the same functions, as for example described in the '388 patent, and no invention is claimed in any specific circuit details.

The modulation signal generator 96 can be conventional also but it is preferred to choose one that is similar to that described in the '388 patent. As explained in connection with FIG. 2 of that patent, the modulator signal waveforms needed to implement the three current modes are created using an oscillator-binary counter and dual multiplexers. Again, no invention is claimed in the present application with respect to the means to generate that function. As is conventional, the RF frequency generator 78 which generates a carrier at the 4 MHz frequency supplies its output via the driver 80 and timer 126 to the input of the RF power amplifier 82. The modulation signal generated by module 96 constitutes one input to the voltage switching regulator 96. One output of the voltage switching regulator 96 is a voltage input to the RF power amplifier 82. Apart from the regulating function, the modulation signal therefore represents a modulated voltage input to the RF power amplifier 82, which also receives the carrier, and thus the output from the latter is the desired modulated carrier. The modulated voltage output of the voltage switching regulator 96 is sampled, by which is meant, that a fraction of the average value of the voltage of the modulated output is then fed back to the input of the voltage switching regulator 96. Another input of the voltage switching regulator 96 also receives a fixed reference voltage. The regulating function is obtained as the switching regulator 96 adjusts its output voltage such that the fed back sample matches the reference or some fixed fraction of the reference. These known voltage switching regulators can easily be adjusted or purchased so that they not only regulate the output voltage but are also are capable of stepping up or boosting the output voltage as in a DC-to-DC converter. So, for example only, if the average output voltage of the voltage switching regulator 96 is, say, 200 volts, and the sample taken is, say, 1/20 of the average output, thus 10 volts, and the reference is, say, 15 volts, then the voltage switching regulator will boost its output voltage to 300 volts, so that the sample matches the reference. The reverse happens if the output voltage drops below the regulated value. This mode of operation of these known voltage switching regulators is taken advantage of in implementing a feature of the invention.

There are three principal inventive features of the present application. The first has already been described in detail, namely the use of the same RF carrier and the same three operating sub-modes for both monopolar and bipolar operation. Specifically, the CUT, CUT/COAG, and HEMO waveforms modulating the same approximately 4 MHz carrier are available at both the monopolar and bipolar output connectors of the unit.

The second and third main features combine to maintain the same maximum output power irrespective of the selection of one of the two cutting modes, namely, the CUT or CUT/COAG operating sub-mode. In the known systems, as the modulation of the carrier varies, the power output also varies. In general, as the modulation increases, as by going from the CUT sub-mode to the CUT/COAG sub-mode, or from the latter to the HEMO sub-mode, the modulation voltage that is supplied to the RF power amplifier 82, also supplied separately with the carrier signal and functioning to combine the latter with the modulating waveform, drops and thus the average output power from the RF power amplifier and thus to the output connectors is correspondingly reduced. To maintain a more constant average power for the two sub-modes involving a cutting function, the voltage switching regulator 96 in combination with an upper voltage divider 98 and a lower voltage divider 100 cooperate in the circumstances described to boost the modulation voltage input to the voltage switching regulator 96 to maintain the average power output from the RF power amplifier 82 substantially constant. The lower voltage divider 100 is fixed to set a minimum voltage feedback, but the upper voltage divider 98 is controlled not only by the power controls 24, 26 by the user on the front panel, but also by the sub-mode controls 20, 22 and the main mode selected by the user. Simply put, a feature of the invention is to control the amount of feedback supplied to the voltage switching regulator 96 as the user selects an operating sub-mode by means of the sub-mode control switch 20 or 22 and the power value by power switches 24, 26, the amount of feedback supplied to the switching regulator 96 is varied which in turn controls the average voltage of the modulation signal inputted to the RF power amplifier 82. There is a direct relation between the feedback to the switching regulator and the degree of modulation. As the modulation increases, reducing the average modulation voltage—thus reducing the output voltage compared to the reference—the feedback boosts the output voltage, thereby contributing to a more constant voltage to the output power amplifier and thus a more constant power, irrespective of the CUT or CUT/COAG operating sub-mode chosen by the user. And, most important, this mode of operation is independent for each of the main monopolar and bipolar modes selected by the user, so that the same maximum output power can be made available in both main modes. The feature is unnecessary for the HEMO sub-mode because the latter typically uses much lower powers than to implement a cutting function. A more detailed explanation of the operation appears below.

The significant inventions of the multiple sub-mode controls, and the production of a more constant average power, rather than constant peak power, in all modes, will be apparent to those skilled in this art from the following detailed description.

Both outputs of the monopolar and bipolar main modes are derived from a conventional single crystal oscillator 78 driving a single RF Power Amplifier 82. Each primary or main mode is capable of providing more than 50 Watts RF output and is matched to the appropriate load impedance by tuned matching sections. The choice between the two modes modes is made by a straightforward footswitch and/or fingerswitch controlled selection relay, operating at low voltage. The monopolar output is matched to a specific unbalanced load, whereas the bipolar output is matched to a specific balanced load—this is conventional. Each of the two main operating modes, monopolar and bipolar, has separate front panel controls for power level and front panel selection of sub-modes CUT (CW), CUT/COAG (series of half sinusoids full wave), and HEMO (intermittent series of half sinusoids-half wave). ON keying of the RF frequency generator 78 is initiated by a fingerswitch 44 or footswitch 40 for monopolar, or the footswitch 42 for bipolar. To provide high overall efficiency; the main DC Power Supply 66 and the final RF Power Amplifier 82 each operates in known switching modes to achieve a variable 4 MHz power with an amplitude modulated output.

The power supply circuit 66, which is conventional, may comprise an input power modular, RFI filter, thermo-fused transformer, and voltage regulator. The mains interface is through a power transformer T1. A full bridge rectifier 68 is connected to the secondary of the transformer to provide the primary DC output power to the final RF power amplifier 82 through the switching regulator 96. The rectified DC supply voltage 95 into the switching regulator has been increased to allow the switching regulator to provide a higher DC voltage, so that higher peak powers in CUT/COAG and HEMO modes are possible. Nominally, a lower voltage is required for the final power amplifier 82 to generate 50 W in the CUT (CW) mode. This arrangement allows a higher output power than the traditional waveform rectifier technique to supply a generally constant output voltage for both cutting modes.

Figure 3:
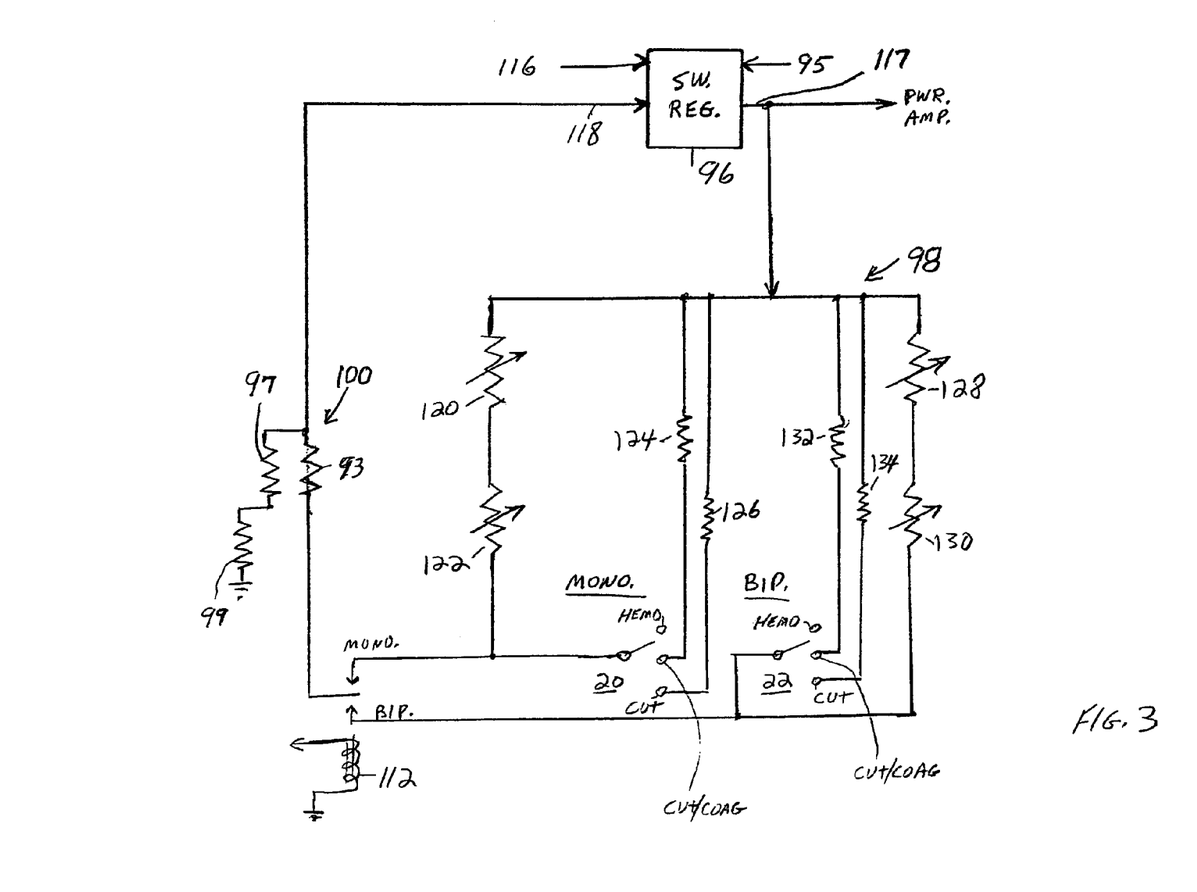
FIG. 3 is a schematic view of one of the modules used in the system of FIG. 2A.

The RF frequency of 4 MHz, which is implemented on both monopolar and bipolar modes, is generated in a packaged crystal oscillator assembly 78, which is enabled by the foot or fingerswitch, shown schematically by arrowed inputs, 104 for the bipolar, 106 for the monopolar footswitch and for the fingerswitch, via a conventional controller 110, which includes or drives one or more relays 112 (see FIG. 3) that selectively activate different sets of contacts to direct the electrosurgical currents to the upper monopolar branch 84, 88, 92, or to the lower bipolar branch 86, 90, 94. The switching regulator 96, which is a commercially-available component, provides the high voltage necessary for the final RF power amplifier 82 to generate the RF output power. Control circuitry for the switching regulator, which includes a reference voltage input 116 and the two voltage dividers 98, 100 sets the output level and, if varied, determines the power output waveform. The single power relay A 112 activated by the footswitch or fingerswitch, selects which of two patient isolation transformers 84, 86 are driven by the RF power amplifier, and as explained below also selects which of two sets of voltage dividers control the feedback to the voltage switching regulator 96. In the monopolar mode, the RF power amplifier is connected to a conventional low impedance primary of the monopolar transformer 84 that works in concert with the matching network 88 to match into a specified nominal monopolar resistive load. For the bipolar mode, a completely separate isolation output transformer 86, a similar matching section 90, and output terminals are utilized. The bipolar matching network is balanced and is matched into its specified nominal bipolar resistive load. This configuration gives sufficient balance to allow the achievement of low leakage current. This arrangement further allows switching between modes to be accomplished at a relatively low voltage to provide matching into two separate load impedances while insuring that only one output is enabled at a time.

The switching regulator 96 provides the desired supply voltage to the RF power amplifier 82 by comparing a sample of the output voltage, taken from output 117, applied at feedback input 118 with its internal reference voltage 116, reducing the output if this voltage tends to rise, or vice-versa. In the preferred application the sample is obtained by a voltage divider 98 arranged to match the reference voltage when the output voltage is corrected. In this application, it operates essentially as a simple divider. Assuming that the unit is set in the monopolar mode, an upper resistor in the voltage divider is made up of potentiometers 120, 122 parallel connected for controlling the output intensity, along with parallel resistors 124, 126, depending on the monopolar sub-mode selected. For CUT the parallel resistor 126 is lowest. For HEMO there is no selected parallel resistor, which sets the voltage to maximum. For CUT/COAG, the parallel resistor 124 is at a medium level. This inverse arrangement takes into account the fact that in the CUT Mode the output is ON continuously, while in HEMO the output is ON intermittently and higher peak powers are required to maintain the average output to its peak power. This parallel arrangement allows any resistor to limit the maximum resistance and thus the maximum output voltage.

There is an identical independent arrangement 128, 130, 132, 134 in the bipolar mode, but the resistor values may or may not be different. Any of the potentiometers 120, 128 parallel connected can be set to minimum to bring the output down regardless of where the other resistors are set. By lowering the composite upper resistance, it reduces the output voltage since the voltage into the feedback loop is raised. The lower voltage divider 100 is represented by fixed resistors 93, and one or two resistors series connected 97, 99. The resistor 97 may not be actually ground. It may be connected to the output of an OP-AMP (not shown), which is capable of driving the low resistor to at least the reference voltage of the switching regulator. This arrangement sets a minimum feedback voltage. (It will be appreciated that the potentiometer 120 is operated by the power control 24, and the potentiometer 128 is operated by the power control 26. The potentiometers 122, 130 are factory adjusted.) Note that in the HEMO sub-mode, the fixed parallel resistors 124,126, 132,134 are omitted from the voltage divider 93. For all three sub-modes, the lower voltage divider 100 is always present in the voltage divider network.

Thus there are two separate independent paths that are used to separately control the feedback and thus the output voltage to the power amplifier 82. The upper resistors 120, 128 at maximum value sets, respectively, the maximum output voltage for the separate main modes selected by the relay 112. Note that when the relay 112 contact is in its upper position, the left or monopolar branch of the voltage divider 98 is active, whereas when the relay 112 contact is in its lower position, the right or bipolar branch of the voltage divider 98 is active The lower resistors 93, 97, 99 can never cause the maximum voltage to be exceeded since it cannot go below ground. This configuration allows the regulator modulator to generate the waveforms for CUT, CUT/COAG and HEMO sub-modes independently in both the monopolar and bipolar main modes. The feedback is schematically represented by arrows 121, 123 in FIG. 2A. While the use of the various resistors to provide a voltage divider network to control the feedback is preferred because it turns out to be relatively inexpensive and reliable, those skilled in this art may be aware of other circuit components that can perform an equivalent function and can be substituted for the voltage divider network, and these other equivalents should be considered included as part of the present invention.

All timing and frequencies, other than the 4 MHz RF frequency, are derived from a conventional binary counter, oscillating at a frequency determined by its external RC circuit. The highest output frequency is the alert frequency to drive a speaker 72 whenever the unit is enabled. It also clocks a timer 78 connected as a 30 second timer (duty cycle). When the timer times out, its output is pulled low opening a voltage supply relay B 124, which disables the drive for the final amplifier 82 and causes the alert tone to be interrupted at a low rate determined by the binary counter at its lowest frequency available.

The binary counter and two multiplexers also make up the modulation signal generator to generate the waveforms required for COAG and HEMO modes and to provide the clock pulse for a programmable timer tracking the duty cycle, as described in the '388 patent. Briefly, as described in the '388 patent, the continuously counting binary generated from the binary counter addresses the input of these two multiplexers which function as a digital/analog converter. Resistors connected to outputs of multiplexers sequentially establish a series of voltage dividers. These resistors have successively lower values, a falling voltage waveform describing one half of an upside down sine wave is generated by the action of one of the multiplexers. The next lower frequency output of the binary counter is taken though an inverter to alternately enable/inhibit the action of another multiplexer. Where one generates a falling portion of a half sine wave, another generates the second, rising, portion using the same resistors This results in a continuous series of half sine waves that is used for the COAG function. Since the required output is continuous, no special waveform is required for CUT. For HEMO, the output of the binary signal is connected through a logical circuit to alternately inhibit both multiplexers by setting all of their addresses to Low, to ultimately generate a series of half sine waves separated by off times (half wave rectifier). This waveform is designed to output the actual desired output voltage independently.

On-Off control and selection of the primary or main mode (monopolar or bipolar) is effected by the fingerswitch 44 or the dual footswitches 40, 42. To meet the isolation requirements, a separate isolated low voltage supply is supplied to the finger switch or the dual footswitches. Either of these will enable a relay and voltage regulators, which in turn enables all of the low level circuits including the driver transistor for the speaker, as well as to the LED indicators and the appropriate circuitry. Also, two exclusive separated relays (not shown) may be used to control the RF output power. One is controlled by the finger switch and monopolar mode of one footswitch, and the other is controlled by the bipolar mode of the other footswitch. Therefore, only one of the two modes can be activated at any one time. This is conventional control circuitry and need not be described in greater detail.

The known CUT, CUT/COAG, and HEMO sub-modes typically are: CUT-CW (full-wave rectified and filtered) output with maximum average power; CUT/COAG-full-wave rectified but unfiltered, deeply modulated, at 37.5 or 75 Hz rate, envelope with approximately 70% average to peak power ratio; HEMO-half-wave rectified and unfiltered, deeply modulated, at 37.5 or 75 Hz rate, envelope with approximately 35% average to peak power ratio.

The RF power generating circuitry may also be of the well known tube-type described in U.S. Pat. No. 3,730,188, whose contents are herein incorporated by reference, which is capable of generating a fully-rectified, filtered RF current for cutting, a full-wave rectified current for combining cutting and coagulation, and a half-wave rectified current for coagulation. Alternatively, the RF power generating circuitry can be of the well-known solid-state type capable of generating the same kinds of waveforms. The RF circuitry, as such, is not part of the present invention, as such circuits are well-known in the prior art. What is a feature of the invention is that the RF circuitry provides the same RF frequency of operation in the 4 MHz range.

In operation, the ground plate 58 is always attached to the patient, and the surgeon can perform any desired monopolar or bipolar electrosurgical procedure. When both the monopolar and bipolar handpieces are plugged into the instrument console 12, then the desired operating conditions for each can be preset as desired. Then whichever handpiece is picked up and operated by the surgeon will automatically determine which is supplied with the appropriate RF currents. Thus, if the bipolar handpiece 56 is selected and the footswitch 42 activated, the bipolar handpiece will be supplied with 4 MHz currents at the power setting selected by the user. On the other hand, if the monopolar handpiece 48 or footswitch 40 is selected and the handpiece fingerswitch 44 activated, the monopolar handpiece will be supplied with 4 MHz currents at the power setting selected by the user. This operates on a first-come, first-served basis, which thus allows the surgeon to use the CUT mode for cutting with the monopolar or bipolar handpiece followed with the bipolar handpiece for closing off any bleeders exposed during the cutting, as one example only.

The construction of the invention, apart from the other benefits described, offers the further advantages of ready accessibility and versatility: accessibility, as the user is able to exercise either handpiece without touching anything else, simplifying greatly maintaining sterile fields; versatility, as the adjustability from one electrosurgical mode to another mode is extremely simple; and importantly substantially constant power output at the main modes and cutting sub-modes selected by the surgeon.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument for selectively providing RF power to operate as main modes both a monopolar handpiece and a bipolar handpiece each in multiple sub-modes including CUT, and HEMO sub-modes, comprising:
   (a) a console unit,
   (b) RF power generating circuitry inside the console and capable of generating electrosurgical currents at a given carrier frequency in the MHz range,
   (c) first electrical connectors at the console for receiving a monopolar handpiece,
   (d) second electrical connectors at the console for receiving a bipolar handpiece,
   e) circuit means for generating first and second different modulation waveforms representing, respectively, the CUT, and HEMO sub-modes,
   f) first means for delivering the first waveform representing the CUT sub-mode to the RF power generating circuitry for modulating the given carrier frequency to produce CUT sub-mode electrosurgical currents,
   g) second means for delivering the second waveform representing the HEMO sub-mode to the RF power generating circuitry for modulating the given carrier frequency to produce HEMO sub-mode electrosurgical currents,
   h) third means for supplying both the CUT and HEMO sub-mode electrosurgical currents to the first electrical connectors,
   i) fourth means for supplying both the CUT and HEMO electrosurgical currents to the second electrical connectors,
   j) whereby both a monopolar handpiece and a bipolar handpiece can be operated at the given frequency in both the CUT and HEMO sub-modes.

2. An electrosurgical instrument according to claim 1, further comprising footswitches and third electrical connectors at a side of the console for connection to the footswitches, said footswitches functioning to turn on and off the RF power generating circuitry.

3. An electrosurgical instrument according to claim 1, wherein the circuit means further comprises means for generating a third different modulation waveform representing the CUT-COAG sub-mode, further comprising fifth means for delivering the third waveform representing the CUT-COAG sub-mode to the RF power generating circuitry for modulating the given carrier frequency to produce CUT-COAG sub-mode electrosurgical currents, the third and fourth means being configured to supply also the CUT-COAG sub-mode electrosurgical currents to both the first and second electrical connectors, whereby both a monopolar handpiece and a bipolar handpiece can be operated at the given frequency in the same CUT, CUT-COAG, and HEMO sub-modes.

4. An electrosurgical instrument according to claim 3, wherein the given frequency is in the range of about 4 MHz.

5. An electrosurgical instrument according to claim 2, further comprising separate plural footswitches, and wherein said monopolar handpiece comprises a fingerswitch, said fingerswitch and one of said footswitches functioning to turn on and off the RF power generating circuitry for the monopolar handpiece, another of said footswitches functioning to turn on and off the RF power generating circuitry for the bipolar handpiece.

6. An electrosurgical instrument according to claim 5, further comprising means for preventing both the footswitch for the bipolar handpiece and the fingerswitch and footswitch for the unipolar handpiece to cause simultaneous supply of electrosurgical currents at both the first and second connectors.

7. An electrosurgical instrument according to claim 1, wherein the console unit comprises separate sub-mode selection switches and separate power control switches for each of the monopolar and bipolar handpieces.

8. An electrosurgical instrument according to claim 7, further comprising a voltage regulator having a reference voltage and outputting an operating voltage to the RF power generating circuitry, the voltage regulator including feedback means to vary its outputted operating voltage such that the average power output remains substantially the same for the different sub-modes of operation.

9. An electrosurgical instrument according to claim 7, further comprising independent means in response to the selection of an operating sub-mode and a power level to vary an operating voltage supplied to the RF power generating circuitry, the independent means being separate for each of the main monopolar and bipolar modes.

10. An electrosurgical instrument according to claim 9 wherein the voltage regulator is a voltage switching regulator, and the feedback means includes a voltage divider.

11. An electrosurgical instrument according to claim 10, wherein the operating sub-modes include the CUT, CUT/COAG, and HEMO modes which each generate modulating waveforms whose average voltage decreases when going from the CUT to the CUT/COAG, and from the CUT/COAG to the HEMO sub-modes, the voltage regulator functioning to boost the operating voltage to the RF power generating circuitry in response to a selected waveform having a lower average voltage.

12. An electrosurgical instrument for selectively providing RF power to operate as main modes both a monopolar handpiece and a bipolar handpiece each in multiple sub-modes including first, second, and third different CUT, CUT/COAG, and HEMO sub-modes, comprising:

(a) a console unit,
(b) RF power generating circuitry inside the console and capable of generating electrosurgical currents at a given frequency in the 4 MHz range,
(c) first means for generating modulated waveforms representative of the different multiple sub-modes and supplying the modulated waveforms to the RF power generating circuitry, the selection of a sub-mode having a tendency to vary the output power from the RF power generating circuitry,
(d) first electrical connectors at the console for receiving a monopolar handpiece,
(e) second electrical connectors at the console for receiving a bipolar handpiece,
(f) second means for controlling the output power of the electrosurgical currents to a maximum level and for supplying the controlled electrosurgical currents at the given frequency in any of the first, second, or third sub-modes to the first electrical connectors for operating in the main monopolar mode,
(g) third means for controlling the output power of the electrosurgical currents to substantially the same maximum level and for supplying the controlled electrosurgical currents at the given frequency in any of the first, second, or third sub-modes to the second electrical connectors for operating in the main bipolar mode,
(h) the second and third means functioning independently in response to selecting the main mode, the first, second, or third sub-mode, and the output power,
(i) whereby all three sub-modes are capable of being supplied to both the monopolar and bipolar handpieces when carrying out their respective procedures.

13. An electrosurgical instrument according to claim 12, wherein the second and third means comprises a voltage switching regulator employing feedback to control its output voltage and means for varying the feedback independently for each of the main modes in response to selecting the sub-mode, or the output power.

14. An electrosurgical instrument according to claim 13, wherein the feedback comprises a voltage divider network configured such that substantially the same maximum output power is produced irrespective of selecting the first, second, or third sub-modes.

15. A method for treating patients with electrosurgical currents from a unitary electrosurgical instrument for selectively providing RF power to operate a monopolar handpiece and a bipolar handpiece each in three separate sub-modes, comprising the steps:

(a) operating the electrosurgical instrument to generate electrosurgical currents in any one of the sub-modes at a single frequency in the 4 MHz range in a procedure for modulating tissue of the patient using a monopolar handpiece,
(b) operating the electrosurgical instrument to generate electrosurgical currents in any one of the same three sub-modes at the same frequency in the 4 MHz range in a procedure for modulating tissue of the patient using a bipolar handpiece.

16. The method of claim 15, wherein the electrosurgical instrument is capable of generating electrosurgical currents in the CUT, CUT/COAG, and HEMO sub-modes, and all three sub-modes are capable of being supplied to both the monopolar and bipolar handpieces when carrying out their respective procedures.

17. The method of claim 16, further comprising using independent power controls for each of the sub-modes, and operating the electrosurgical instrument such that the maximum output power is substantially the same irrespective of whether the CUT, CUT/COAG, or HEMO sub-mode is selected.

* * * * *